United States Patent [19]
Kimbara et al.

[11] Patent Number: 5,897,996
[45] Date of Patent: Apr. 27, 1999

[54] METHOD FOR DEGRADING POLYCHLORINATED BIPHENYLS AND NOVEL MICROORGANISM

[75] Inventors: Kazuhide Kimbara; Minoru Shimura, both of Tokyo; Takashi Hatta, Okayama; Hohzoh Kiyohara, Bizen, all of Japan

[73] Assignee: Railway Technical Research Institute, Tokyo, Japan

[21] Appl. No.: 09/048,306

[22] Filed: Mar. 26, 1998

[30] Foreign Application Priority Data

Jun. 23, 1997 [JP] Japan ................................. 9-166373

[51] Int. Cl.$^6$ ................................. C12N 1/20; B09B 3/00
[52] U.S. Cl. ................................. 435/262.5; 435/252.1
[58] Field of Search ................................. 435/262.5, 252.1

[56] References Cited

PUBLICATIONS

Wu et al Applied & Envir. Microbiol. Nov. 1996 vol. 62 No. 11 pp. 4174–4179.
Biotech Abstract 89–05760 Biotox AU8775287 Jan. 05, 1989.

*Primary Examiner*—Herbert J. Lilling
*Attorney, Agent, or Firm*—Finnegan, Henderson, Farabow, Garrett & Dunner, L.L.P.

[57] ABSTRACT

According to this method for degrading PCBs by utilizing thermophilic bacteria possessing the capability of degrading PCBs, the degradation of PCBs is quick, thereby enabling processing devices to be made more compact and shortening the processing time. As a microorganism suitable for use in this method, Bacillus sp. JF8, a thermophilic microorganism which possesses the capability of degrading PCBs, is offered.

7 Claims, 2 Drawing Sheets

METHOD FOR DEGRADING POLYCHLORINATED BIPHENYLS AND NOVEL MICROORGANISM

BACKGROUND OF THE INVENTION

1. Field of the Invention

The present invention relates to a method for degrading polychlorinated biphenyls, and more specifically to a method for degrading polychlorinated biphenyls using thermophilic bacteria and to a novel microorganism possessing the ability to degrade polychlorinated biphenyls.

This application is based on Patent Application No. Hei 9-166373 filed in Japan, the content of which is incorporated herein by reference.

2. Description of Related Art

Biological degradation of polychlorinated biphenyls (hereinafter abbreviated to PCBs) utilizing bacteria which possess the ability to breakdown PCBs into simple non-toxic compounds is a conventional method for decomposing PCBS.

Research has been advanced for the practicalization of PCB degradation methods using microorganisms, because they enable PCBs to be processed to low concentrations without releasing harmful degradation products during degradation, and because they allow processing with more advantageous conditions in comparison to physical PCB treating methods such as high-temperature incineration or ultraviolet degradation in consideration of costs and processing equipment.

The present applicant has invented novel microorganisms capable of degrading organic chlorine compounds such as PCBs, and methods for degrading organic chlorine compounds using these microorganisms, and has previously filed patent applications relating thereto under Japanese Patent Application No. Hei 7-42201 and Japanese Patent Application No. Hei 8-35284.

The conventional art, including the novel microorganism described in the specifications of the above-mentioned applications, have problems in that the degradation of PCBs is slow because the PCB-degrading bacteria are cultured at room temperature (30–37° C.).

SUMMARY OF THE INVENTION

The present inventors focused on thermophilic bacteria which generally have rapid growth rate, and have identified a thermophilic bacteria which can grow and degrade PCBs at temperatures of approximately 60° C., and offer a PCB degradation method using these bacteria.

The method for degrading polychlorinated biphenyls according to the present invention comprises steps of adding polychlorinated biphenyls to a culture medium for thermophilic bacteria; and culturing thermophilic bacteria possessing the capability of degrading polychlorinated biphenyls in said culture medium.

The novel microorganism used in the present invention is Bacillus sp. JF8 possessing the ability to degrade polychlorinated biphenyls.

The above-mentioned Bacillus sp. JF8 has already been deposited at the International Depository Authority, and has been assigned the International Deposit Number FERM BP-6098.

The present invention offers for the first time thermophilic bacteria which are capable of degrading PCBs.

Additionally, since the method for degrading PCBs using these thermophilic bacteria enables quick degradation of PCBs, processing devices can be made more compact. Additionally, the processing time can be shortened, so as to increase the processing efficiency.

Additionally, since the bacteria grow in a high-temperature culture, it is possible to simplify sterilization procedures to prevent the contamination by stray bacteria, thus allowing a reduction in the cost of processing devices used for degradation.

DESCRIPTION OF THE PREFERRED EMBODIMENTS

Figure 1:
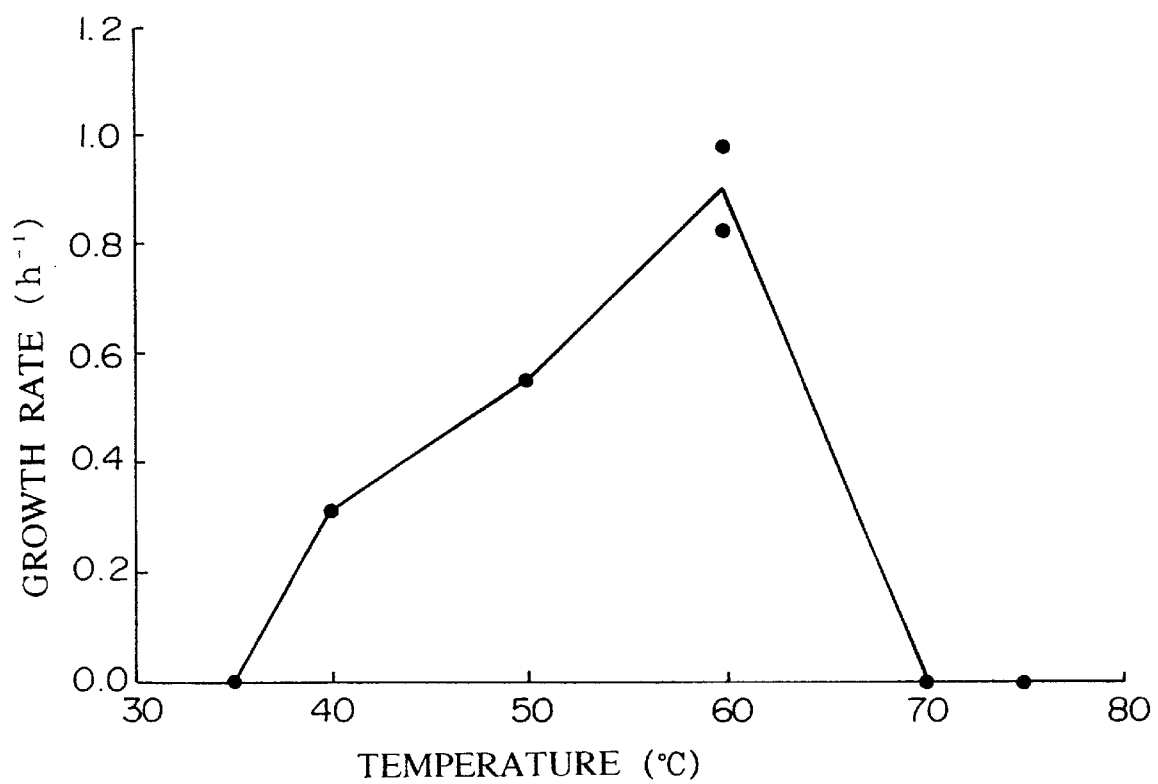
FIG. 1 is a graph showing the temperature dependence of the growth of the bacterial strain used in the present invention.

The method for degrading PCBs according to the present invention is characterized by culturing thermophilic bacteria, especially PCB-degrading bacteria belonging to the genus Bacillus, at a culturing temperature of 45–70° C., more preferably 50–65° C., in order to degrade PCBs added to the culturing medium at a high rate of efficiency.

The degradation of PCBs by microorganisms is by specific enzymatic reactions. The intermediate products and final products are known, and there are no problems with regard to the safety of the method for degrading PCBs according to the present invention.

The PCB-degrading bacteria belonging to the genus Bacillus used in the present invention, is a bacterial strain which live and grow under temperature conditions of 45–70° C., preferably 50–65° C., using as their sole carbon source biphenyls which are the carbon skeletons of PCBs, found in compost or the like. The present inventors have isolated thermophilic bacteria possessing the ability to degrade PCBs (Bacillus sp. JF8), as shall be described in the examples given below.

When working the method for degrading PCBs according to the present invention, it is possible to use these isolated thermophilic bacteria, or to use other newly isolated thermophilic bacteria.

In order to degrade PCBs using these thermophilic bacteria possessing the ability to degrade PCBs, the bacteria can be cultured by using an appropriate culture medium, for example a liquid culture medium for isolation of thermophilic bacteria containing a small amount of casamino acid and yeast extract, with biphenyl as the growth substrate, adding PCBs, and culturing at 45–70° C., preferably 50–65° C., more preferably at 60° C. This culture should be cultivated under aerobic conditions by shaking or agitating the culture container, or aerating the medium. The form of the culture container is not particularly restricted, and it is possible to use anything from laboratory-level flasks to large-scale culture tanks.

Since these thermophilic bacteria possessing the ability to degrade PCBs are capable of degrading substrates such as naphthalene and dibenzofuran as well as biphenyls and PCBs, they can also be applied to the degradation and disposal of these chemicals.

The PCBs which can be degraded by these bacteria are monochlorobiphenyls, dichlorobiphenyls and trichlorobiphenyls having less than four substituent chlorine atoms. The thermophilic bacteria is incapable of degrading PCBs having four or more substituent chlorine atoms. When PCBs having four or more substituent chlorine atoms are included, they can be degraded by first irradiating with ultraviolet light to make the number of substituent chlorine atoms less than four, then adding to the culture.

Since this PCB degradation method using thermophilic bacteria is capable of quickly degrading PCBs, the processing devices can be made more compact. Additionally, the processing time can be shortened, thus improving the processing efficiency.

Additionally, contamination by other bacteria is prevented due to the high-temperature of the culture medium, so that sterilization procedures can be simplified, thereby reducing the cost of processing devices used in degradation.

EXAMPLES

1. Purpose:

For the purpose of improving the PCB degrading efficiency of PCBs using microorganisms, the present inventors have considered thermophilic bacteria which generally have a high growth rate in order to obtain thermophilic bacteria possessing PCB degrading ability, and consequently have isolated and analyzed thermophilic bacteria which degrade PCBs.

2. Isolation of Bacteria Which Degrade Biphenyls:

Since PCBs do not exist naturally and are extremely resistant to biodegradation, it is difficult to find bacteria capable of degrading PCBs directly. Therefore, the carbon source used was biphenyl ($C_6H_5 \cdot C_6H_5$) which are the carbon skeletons of PCBS, and a search was made for bacteria capable of assimilating this compound.

A test sample collected from compost was added to a liquid culture medium for isolating thermophilic bacteria containing 0.02% casamino acid and 0.01% yeast extract, then the bacteria were cultured by shaking at 60° C. with biphenyls as the sole carbon source. After enrichment culturing for approximately two months while supplementing water which was evaporated, a number of strains which grow by degrading biphenyls as their sole carbon source were isolated. Among these, the strain JF8 which grows abundantly in a biphenyl culture was selected. In order to find biphenyl degrading bacteria, these bacteria produce a yellow meta-cleavage substance which is the metabolic product of biphenyls, and this yellow color was used as an indicator of biphenyl degrading ability.

3. Identification of Isolated Bacteria:

The characteristics of the thermophilic bacteria JF8 possessing the ability to degrade a biphenyl were studied. On studying the shape with a scanning electron microscope, this strain was found to consist of rod-shaped bacteria having a width of approximately 1 μm and a length of approximately 2.5–5 μm. Additionally, the bacteria were gram-positive spore-forming rod-shaped bacteria, which actively formed spores even in liquid culture media.

The results of an analysis of the physiological properties of the JF8 strain are shown in Table 1.

TABLE 1

| | JF8 |
|---|---|
| Shape | rod-shaped |
| Width (μm) | 0.9–1.1 |
| Length (μm) | 2.5–5.0 |
| Spores | oval-shaped |
| Catalase Activity | + |
| Anaerobic Growth | − |
| Growth Temperature (°C.) | 35–70 |

TABLE 1-continued

| | JF8 |
|---|---|
| Growth at pH 5.7 | − |
| 16Sr DNA Homology | B. stearothermophilus (97.8%) |
| Fatty Acid Homology | Bacillus sp. |

As shown in Table 1, the bacteria had a growth temperature of 35–70° C. and the base sequence of 16S ribosomal DNA was 97.8% homologous to that of *B. stearothermophilus*, indicating that the bacteria was closely related to *Bacillus stearothermophilus* (according to a comparison on the database of the DSM (Deutsche Sammlung von Mikroorganismen) library). An analysis of fatty acids indicated a good homology with Bacillus (also based on a comparison on the database of the DSM library).

Upon overall consideration of the above-mentioned physiological properties, JF8 was found to belong to Group 5 of the Bacillus genus. Therefore, the present inventors named the isolated bacterial strain Bacillus sp. JF8.

Subsequently, PCB degradation experiments were conducted using the JF8 strain.

4. Physiology:

Using the JF8 strain, the temperature dependence of growth with biphenyls as the carbon source was studied. The basic culture medium was an inorganic medium for thermophilic bacteria, to which was added 0.01% of casamino acid and 0.02% of yeast extract. In order to obtain bacteria in the growing stage, the culture was cultivated under conditions of 60° C. for six hours, and the culture was seeded with the pre-culture medium at 2%. 1 L of the present culture was put into a 2 L fermenter in order to measure the growth. The results are shown FIG. 1.

FIG. 1 is a graph showing the relationship between the growth rate and culture temperature when biphenyls are used as the carbon source. The temperature conditions studied were 35° C., 40° C., 50° C., 60° C., 70° C. and 75° C. The growth of bacteria was monitored by collecting small amounts of the culture medium and measuring the light absorbance at 650 nm.

The growth of bacteria was not observed at 35° C., 70° C. and 75° C. even after culturing for 24 hours. The best growth was at 60° C., and this temperature can be considered to be the optimum temperature for this bacteria.

In similar experiments in a nutrient culture medium, the optimum temperature was observed to be 60° C. and growth was observed at 70° C.

To study the ability of this thermophilic bacteria to assimilate aromatic compounds similar to biphenyls, growth in different carbon sources was monitored. The results are shown in Table 2.

TABLE 2

| Substrate | Growth |
|---|---|
| Biphenyl | + |
| p-Chlorobiphenyl | + |
| Benzene | − |
| Benzoic Acid | + |
| Toluene | − |
| Naphthalene | + |
| Anthracene | − |
| Phenanthrene | − |
| Dibenzofuran | + |

Table 2 shows whether or not growth was observed when each substrate was used as a carbon source.

In the results shown in Table 2, it is notable that the bacteria were able to grow even in para-chlorobiphenyl which is a monochloride of biphenyl. Benzoic acid is a metabolic product of biphenyls. The bacteria grew in naphthalene as well. On the other hand, growth was not observed in either benzene or toluene.

5. Degradation of PCBs:

Next, the ability to degrade PCBs which are polychlorides of biphenyl was studied. The container used for the culture was an baffled Erlenmeyer flask of 300 ml capacity, which was sealed with a screw-on cap in order to prevent the PCBs from leaking. 50 ml of a culture medium for thermophilic bacteria was put into the flask, which was seeded with 2% of a JF8 strain culture, and it was cultured under temperature conditions of 60° C. First, the bacteria were cultured for 24 hours with only biphenyls, then a PCB with trichlorinated biphenyls as the main component, Kaneclor 300 (trade name, manufactured by Kaneka Corp.), was added at a concentration of 20 $\mu$g/ml. Then, the culture was continued for 48 hours, after which the substances capable of being extracted by ethyl acetate were analyzed by GC/MS (gas chromatography/mass spectrometry).

Figure 2:
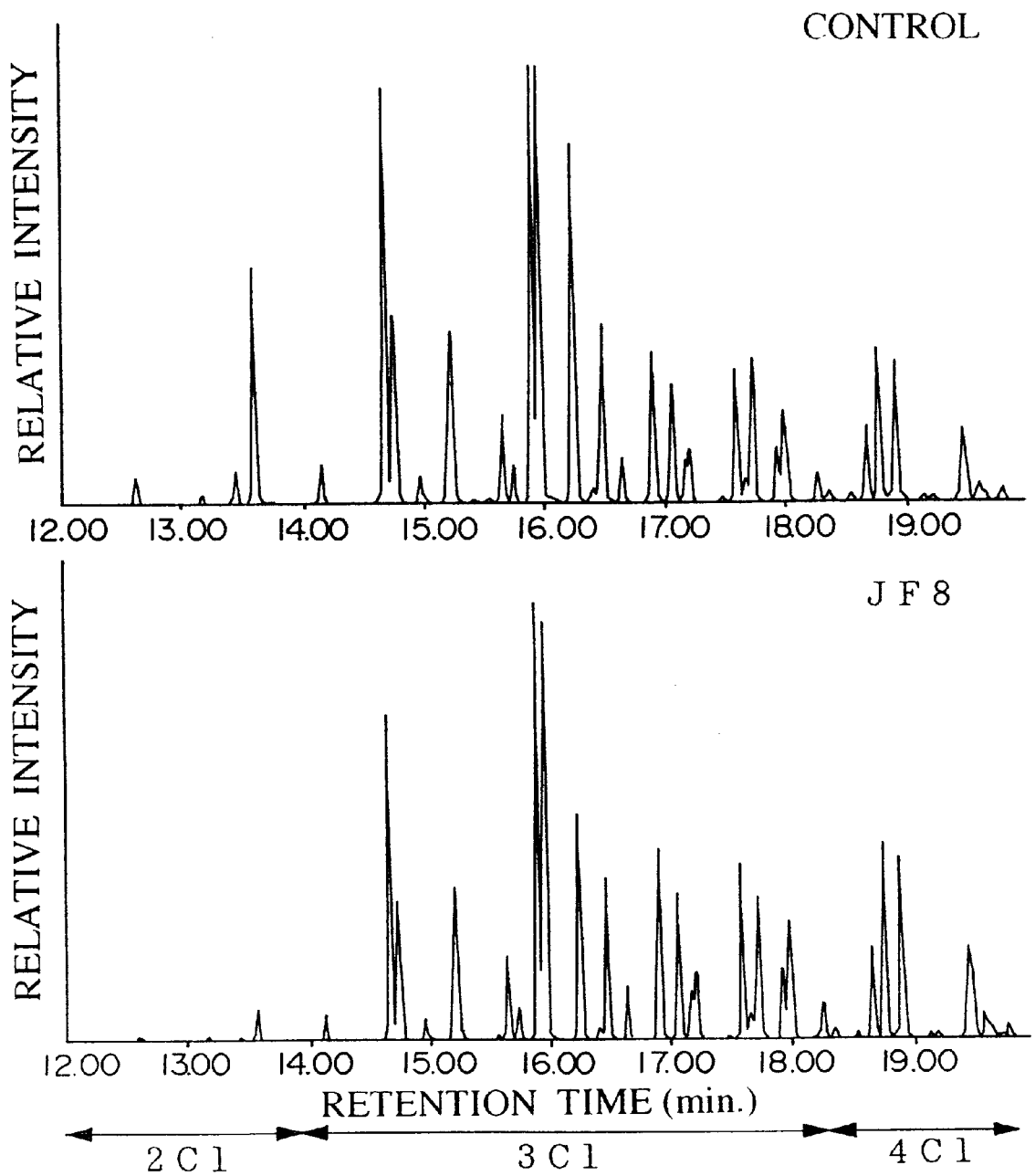
FIG. 2 is a graph showing the PCB degrading ability of the bacterial strain used in the present invention.

FIG. 2 shows the results of this PCB degradation test. The top plot shows the results of the culture meduim prior to degradation (control), while bottom plot shows the results of the culture medium in which JF8 was grown for 48 hours. Each peak corresponds to each PCB congener in Kaneclor 300. The arrows in the bottom plot indicate the rough distribution in the number of chlorine substitution (dichloro, trichloro, or tetrachloro biphenyls). On comparing the top and bottom peak patterns, it is observed that some peaks have been reduced such as the following representative peaks.

13.5 min 2,4'-dichlorobiphenyl; 89% reduced 14.68 min 2,5,2'-trichlorobiphenyl; 38% reduced 16.25 min 3,4,2'-, 2,3,4-, and 2,3,3'-trichlorobiphenyls; 49% reduced 16.5 min 2,3,4'-trichlorobiphenyl; 33% reduced In total, a 68.8% reduction was observed in dichlorobiphenyls and a 32.1% reduction was observed in trichlorobiphenyls. The tetrachlorobiphenyls were only reduced by 1.18% and was left almost totally undegraded. Additionally, upon analyzing the GC/MS degradation products, chlorobenzoic acids were detected, thus indicating that the PCBs were degraded by the thermophilic bacteria.

As mentioned above, the present inventors have been the first to isolate a thermophilic bacteria capable of growing with biphenyls as the sole carbon source. These bacteria are classified as belonging to Group 5 in the Bacillus genus, and they have been observed to be capable of growing at temperatures of around 60° C., and growing even on aromatic compounds such as naphthalene in addition to biphenyls. Additionally, the ability of a thermophilic bacteria to degrade PCBs was confirmed for the first time.

What is claimed is:

1. A method for degrading polychlorinated biphenyls, comprising steps of:

adding polychlorinated biphenyls to a culture medium for thermophilic bacteria: and culturing thermophilic bacteria possessing a capability of decomposing polychlorinated biphenyls in said culture medium under an aerobic condition.

2. A method for degrading polychlorinated biphenyls in accordance with claim 1, wherein the thermophilic bacteria is capable of growing substantially with biphenyls as a sole carbon source.

3. A method for degrading polychlorinated biphenyls in accordance with claim 1, wherein the thermophilic bacteria are polychlorinated-biphenyl-degrading bacteria which belong to the genus Bacillus.

4. A method for degrading polychlorinated biphenyls in accordance with claim 3, wherein the thermophilic bacteria are Bacillus sp. JF8.

5. A method for degrading polychlorinated biphenyls in accordance with claim 1, wherein the culturing is performed at a temperature of 45–70° C.

6. A method for degrading polychlorinated biphenyls in accordance with claim 5, wherein the culturing is performed at a temperature of 50–65° C.

7. A method for degrading polychlorinated biphenyls in accordance with claim 1, wherein the polychlorinated biphenyls are subjected to ultraviolet irradiation to dechlorinate higher chrorinated congeners which contain 4 or more chlorine per biphenyl atom, so as to have a polychlorinated biphenyl solution with less than four substituent chlorines per biphenyl atom prior to addition of the polychlorinated biphenyls to the culture medium.

* * * * *